United States Patent [19]

Shroot et al.

[11] Patent Number: 4,755,530
[45] Date of Patent: Jul. 5, 1988

[54] 1-HYDROXY-8-ACYLOXY-10-ACYL ANTHRONES, PROCESS FOR THEIR PREPARATION AND THEIR USE IN HUMAN OR VETERINARY MEDICINES AND IN COSMETIC FORMULATIONS

[75] Inventors: Braham Shroot, Antibes; Gerard Lang, Saint Gratien; Jean Maignan, Tremblay les Gonesse, all of France

[73] Assignee: Centre International de Recherches Dermatologiques (C.I.R.D), Valbonne, France

[21] Appl. No.: 852,822

[22] Filed: Apr. 16, 1986

[30] Foreign Application Priority Data

Apr. 17, 1985 [FR] France ............... 85 05785

[51] Int. Cl.$^4$ .................... A61K 31/12; C07C 50/16
[52] U.S. Cl. .................... 514/510; 260/351
[58] Field of Search .................. 260/351; 514/510

[56] References Cited

U.S. PATENT DOCUMENTS

| | | | |
|---|---|---|---|
| 2,530,065 | 11/1950 | King .................... | 560/39 |
| 2,574,150 | 11/1951 | Kerwin et al. ............ | 260/501.18 |
| 3,198,802 | 8/1965 | Clark et al. ............. | 560/38 |
| 4,107,186 | 8/1978 | Petrack et al. ........... | 260/351 |
| 4,299,846 | 11/1981 | Mastakallio et al. ....... | 260/351 |

FOREIGN PATENT DOCUMENTS

| | | | |
|---|---|---|---|
| 743137 | 9/1966 | Canada .................. | 564/426 |
| 0033075 | 1/1980 | European Pat. Off. ...... | 260/351 |
| 0017420 | 10/1980 | European Pat. Off. ...... | 260/351 |
| 2140007 | 11/1984 | United Kingdom .......... | 260/351 |

OTHER PUBLICATIONS

Hrabowskai, M. et al., "Antitumor Activity of 1-Nitro-9-Aminoacridine Derivatives", Arzneium-Forsch/Drug Res., 32(11), No. 9, (1982), pp. 1013–1016.

Chemical Abstracts, vol. No. 13, 9/30/74, p. 443, No. 7722s, Hofer et al., "Acylation of 1,8-Dihydroxy-9-Anthrones" & Pharm. Acta Helv., 1974, 49(i), 35-37.

*Primary Examiner*—Glennon H. Hollrah
*Assistant Examiner*—Raymond Covington
*Attorney, Agent, or Firm*—Cushman, Darby & Cushman

[57] ABSTRACT

1-hydroxy-8-axyloxy-10-acyl anthrones have the formula

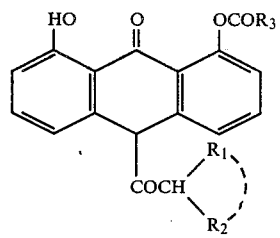

wherein
  $R_1$ represents hydrogen or linear lower alkyl,
  $R_2$ represents hydrogen, linear or branched alkyl having 1–6 carbon atoms, or linear or branched alkenyl having 2–6 carbon atoms, or $R_1$ and $R_2$ together with the carbon atom to which they are attached form a cycloalkyl radical having 3–6 carbon atoms,
  $R_3$ represents linear or branched alkyl having 1–6 carbon atoms, linear or branched alkenyl having 2–6 carbon atoms, cycloalkyl having 3–6 carbon atoms, 2- or 3-furyl, 3- or 4-pyridyl or 2-thienyl.

7 Claims, No Drawings

1-HYDROXY-8-ACYLOXY-10-ACYL ANTHRONES, PROCESS FOR THEIR PREPARATION AND THEIR USE IN HUMAN OR VETERINARY MEDICINES AND IN COSMETIC FORMULATIONS

The present invention relates to novel 1-hydroxy-8-acyloxy-10-acyl anthrones, which are derivatives of 1,8-dihydroxy-9-anthrone on anthralin, to a process for their preparation and to their use in human or veterinary medicines and in cosmetic formulations.

In human or veterinary therapy, the novel compounds of the present invention are useful as antiproliferative agents which can be employed principally in the treatment of psoriasis and warts, or they are useful as anti-inflammatory agents that can be employed in the treatment of rheumatism, dermatoses and eczema.

When present in cosmetic formulations, the compounds of the present invention are useful as antiacne, antipellicular and antiseborrheic agents. They are also useful in combatting hair-fallout.

The 1-hydroxy-8-acyloxy-10-acyl anthrones of the present invention exhibit, relative to anthralin and certain known anthralin derivatives such as those described in U.S. Pat. No. 4,299,846, the advantage of being less irritating, more stable and causing less staining of the skin and clothing, principally in basic washing.

The 1-hydroxy-8-acyloxy-10-acyl anthrones are, moreover, more active than the compounds described in German Pat. No. 2.154.609.

The 1-hydroxy-8-acyloxy-10-acyl anthrones of the present invention can be represented by the following formula

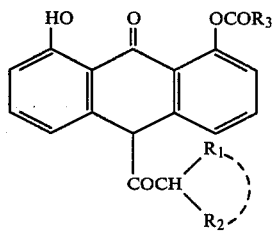

(I)

wherein $R_1$ represents hydrogen or linear lower alkyl, $R_2$ represents hydrogen, linear or branched alkyl having 1–6 carbon atoms, linear or branched alkenyl having 2–6 carbon atoms, or $R_1$ and $R_2$ together with the carbon atom to which they are attached form a cycloalkyl group having 3–6 carbon atoms, $R_3$ represents linear or branched alkyl having 1–6 carbon atoms, linear or branched alkenyl having 2–6 carbon atoms, cycloalkyl having 3–6 carbon atoms, a 2- or 3-furyl radical, a 3 or 4-pyridyl radical or a 2-thienyl radical.

By linear lower alkyl is meant a radical having 1–4 carbon atoms.

Representative linear or branched alkyl radicals in the meansings of $R_2$ and $R_3$, include, principally, methyl, ethyl, propyl, isopropyl, butyl, isobutyl, tert.butyl, pentyl or isopentyl radicals.

Representative linear or branched alkenyl radicals having 1–6 carbon atoms include allyl, 1-propenyl or 2-propenyl radicals.

When the $R_1$ and $R_2$ radicals together form a cycloalkyl radical, preferably the cycloalkyl is cyclopentyl or cyclohexyl.

Representative compounds of Formula (I) include, particularly:
1-hydroxy-8-acyloxy-10-acetyl anthrone,
1-hydroxy-8-acetoxy-10-cyclohexylcarbonyl anthrone,
1-hydroxy-8-isobutyryloxy-10-propionyl anthrone,
1-hydroxy-8-acetoxy-10-propionyl anthrone,
1-hydroxy-8-propionyloxy-10-propionyl anthrone and
1-hydroxy-8-isobutyryloxy-10-cyclohexylcarbonyl anthrone.

The present invention also relates to a process for the preparation of the 1-hydroxy-8-acyloxy-10-acyl anthrones of Formula (I) above.

These compounds are prepared in accordance with the following reaction scheme:

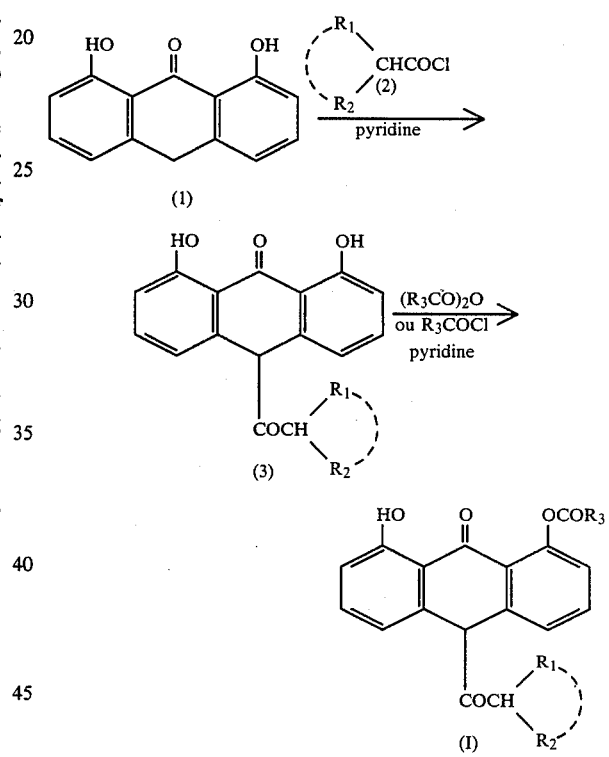

The first step of this synthesis comprises reacting 1,8-dihydroxy-9-anthrone (1) or anthralin with an acid chloride (2) in the presence of a base such as pyridine, the reaction being carried out in an organic solvent such as toluene under a nitrogen atmosphere and in the absence of light or the humidity of air.

It is believed that the acid chloride employed, having a proton in a position α to the carbonyl, forms a ketene intermediate which reacts with the 1,8-dihydroxy anthrone so as to lead to an adduct which is then transformed into the 10-acyl derivative of formula (3).

The second step of the process of the present invention comprises treating the 1,8-dihydroxy-10-acyl anthrone (3) with an acide anhydride of the formula $(R_3CO)_2O$ either alone, or in admixture in an organic solvent, such as toluene, or as an alternative with an acid chloride, $R_3COCl$, when the corresponding anhydride is difficult to obtain.

In order to obtain in a preferred manner, the (3) derivative monoacylated in the 10-position, it is necessary to use an excess of acid chloride relative to the anthralin, this excess being about 1.5–3 equivalents.

Moreover, due to the nature of the acid chloride it is preferable to add the pyridine and the acid chloride in two stages or portions in order to limit the formation of di- or tri-acylated products and to terminate the reaction when the anthralin has been transformed into the expected product monoacylated in the 10-position.

The base employed in the first step of the present process, such as pyridine, must also be used in excess relative to the anthralin, an excess of 1.8 to 3.2 equivalents being considered particularly desirable.

After the addition of the first portion of the pyridine and acid chloride, the temperature of the reaction mixture is raised to about 80°–90° C. for 30 minutes to 2 hours. Then, after cooling, the reaction mixture to ambient temperature, there is added thereto a complementary amount of pyridine and the remainder of the acid chloride. The reaction mixture is again raised to a temperature of about 80°–90° C. for 1 to 2 hours until the anthralin has completely disappeared. The first step of the present invention can be effected in a more dilute medium and in this situation the reaction will be carried out at ambient temperature by adding all of the pyridine (preferably 1.5 to 2 equivalents) in a single charge at the beginning of the reaction.

After cooling the reaction mixture the pyridinium hydrochloride formed is removed by filtration or extraction with water and the toluene phase is then concentrated to about 1/5 of its initial volume.

Thereafter, the expected product is purified by silica gel chromatography.

The 1,8-dihydroxy-10-acyl anthrones (3) are generally entrained in the first elution fractions. Then, using a solvent or a mixture of solvents of increasing polarity, the mono-, di- and tri-acyloxy 10-acyl derivatives that are eventually formed during the course of the reaction are entrained.

In certain instances, the derivative monoacylated in the 10-position can be isolated by recrystallization without it being necessary to utilize chromatography techniques.

In the second step of the present invention when there is employed either an acid anhydride or an acid chloride easily removable by evaporation, the reaction is conducted without a solvent and in the presence of a large excess of the reactants at a temperature between 80° and 150° C.

However, a reaction solvent such as toluene can be employed when the acid anhydride or the acid chloride has a high boiling point, which facilitates their removal by evaporation under a vacuum.

The reaction is then conducted at a temperature between 70° and 100° C.

The evolution or progress of the reaction is followed by thin layer chromatography and the reaction is terminated as soon as the disappearance of the initial reactant and the preponderant formation of the 1-hydroxy-8-acyloxy-10-acyloxy-10-acyl anthrone are observed.

After the end of the reaction, water is poured into the reaction mixture which is then subjected to various washings, principally with sodium bicarbonate solutions. The toluene phase is then dried on magnesium sulfate and filtered. The resulting expected product is then purified by recrystallization, or by silica gel chromatography using preferably toluene or a tolueneethylacetate mixture as the eluant.

In general, the non-transformed initial reactant is entrained at the head of the chromatography, followed then by the derivatives di-acylated in the 8- and 10-positions and finally in certain cases by derivatives tri-acylated in the 1-, 8- and 10-positions.

The yields of 1-hydroxy-8-acyloxy-10-acyl anthrone are in general between 20 and 50 percent relative to the 1,8-dihydroxy-10-acyl anthrone.

The present invention also relates the use of the compounds of Formula (I) in human or veterinary medicine and in cosmetic formulations.

In human or veterinary therapy, the compounds according to the present invention are powerful antiproliferative agents, principally in the treatment of psoriasis and warts, and excellent anti-inflammatory agents principally in the treatment of rheumatism, dermatoses and eczema.

In cosmetic formulations, the compounds according to the present invention can be employed in the treatment of acne, pellicules, seborrhea, and in combatting falling out of hair.

The cosmetic or pharmaceutical compositions can be prepared, for example, by adding the active compound of Formula (I), in an amount between 0.1 and 5 percent, in various inert, non-toxic supports, solid or liquid, which are conventionally employed in compositions having a cosmetic or therapeutic use.

The pharmaceutical compositions can be administered enterally, parenterally or topically. For enteral administration, the compositions can be provided in the form of tablets, powders, granules, gelules, pills, syrups, suspensions or solutions.

The posology will depend on the manner of administration selected and the activity sought.

The pharmaceutical compositions can also contain inert or ultimately pharmacodynamic active components. The tablets or granules can contain for example, binders, fillers, supports or diluents.

Liquid compositions can be provided, for example, in the form of a sterile solution miscible with water. In addition to the active compound, the gelules can contain a filler or a thickening agent. The orally administrable pharmaceutical compositions can also contain agents to improve their flavor, as well as conventionally employed adjuvants such as preservatives, stabilizers, regulators and emulsifiers. Salts and buffers can also be included in these compositions.

The supports and diluents such as those set forth above can comprise organic or mineral substances, for example, gelatine, lactose, starch, magnesium stearate, talc, gum arabic, vegetable and mineral oils, fillers, thickening agents, dyes, humectants or polyalkylene glycols.

When the pharmaceutical compositions are intended for topical application, they can be provided in the form of an ointment, salve, gel, dye, cream, solution, lotion, micronized powder, spray, suspension, shampoo or inhibited buffer.

The ointments and salves are preferred and are prepared by admixing the active compound according to the invention with nontoxic, inert supports appropriate for topical treatment.

The following non-limiting examples of the preparation of the compounds according to the invention and of pharmaceutical and cosmetic compositions are given to illustrate the present invention.

EXAMPLE 1

Preparation of 1-hydroxy-8-acyloxy-10-acyl anthrone (a) 1,8-dihydroxy-10-acetyl anthrone To a solution of 56.5 g of purified anthralin (0.25 mole) in 1750 cm$^3$ of anhydrous toluene, there are added, with stirring at ambient temperature, 27.3 cm$^3$ of anhydrous pyridine (0.34 mole). There are then slowly added, using a dropping funnel, 21.4 cm$^3$ of acetyl chloride (0.3 mole). There is produced during the course of this addition a slight exothermicity. After the end of the addition, the temperature of the reaction mixture is raised to 90° C. for about 1 hour. After cooling the reaction mixture there are added at 30°–35° C., 27.3 cm$^3$ of pyridine and then slowly 21.4 cm$^3$ of acetyl chloride. The mixture is stirred for 1 hour at 85°–90° C. After having verified that the anthralin has been transformed into the 10-acetyl derivative, the reaction mixture is brought to ambient temperature, then washed three times with water (250 cm$^3$). The toluene phase is decanted, dried on sodium sulfate and then concentrated to about 300 cm$^3$. This solution is then introduced into a silica gel column and eluted with toluene and a 1:1 toluene-methylene chloride mixture. The first fractions are collected and concentrated under a vacuum. The resulting solid is then recrystallized in toluene, yielding 21 g of bright yellow crystals of 1,8-dihydroxy-10-acetyl anthrone having a melting point of 146° C.

Elemental Anaylsis: $C_{16}H_{12}O_4$: Calculated: C: 71.63; H: 4.51; O: 23.85. Found: C: 71.44; H: 4.43; N: 23.97

(b) 1-hydroxy-8-acetoxy-10-acyl anthrone

A stirred solution of 3 g of 1,8-dihydroxy-10-acetyl anthrone, obtained above, in 20 cm$^3$ of acetic anhydride, is brought, under an inert atmosphere in the absence of light, to a temperature between 85° and 95° C. for 4½ hours. The solution is then concentrated under reduced pressure. The resulting product is dissolved in 30 cm$^3$ of methylene chloride and the solution is introduced into a silica gel column. On elution with methylene chloride, there is isolated in the first fractions 0.8 g of the non-transformed initial reactant. Then, on elution with a 95/5 mixture of methylene chloride-ethyl acetate, the expected product is isolated.

After concentration of the solvent and recrystallization is isopropyl ether, 1.3 g of 1-hydroxy-8-acetoxy-10-acetyl anthrone in the form of yellow crystals having a melting point of 128° C. are obtained.

Elemental Analysis: $C_{18}H_{14}O_5$: Calculated: C: 69.67; H: 4.55; O: 25.78. Found: C: 69.14; H: 4.60; O: 26.08.

EXAMPLE 2

Preparation of 1-hydroxy-8-acetoxy-10-cyclohexyl carbonyl anthrone (a) 1,8-dihydroxy-10-cyclohexylcarbonyl anthrone To a solution of 50 g of anthralin (0.22 mole) in 2 liters of anhydrous toluene and 44 cm$^3$ of pyridine, there are added, over a 30 minute period at ambient temperature and with stirring, 44 cm$^3$ of cyclohexane carboxylic acid chloride (1.5 mole).

The reaction mixture is stirred at ambient temperature for 4 hours.

The precipitated pyridinium hydrochloride is removed by filtration, then washed with toluene. The toluene filtrates are evaporated under reduced pressure and the solid residue is dissolved in 2 liters of dichloromethane.

The resulting solution is washed initially with 500 cm$^3$ of acidulated water and then tree times with water and finally dried on sodium sulfate.

After evaporation of the solvent under reduced pressure a solid is obtained which is dissolved cold in 150 cm$^3$ of 1,2-dichloroethane. The resulting solution is filtered, then cooled using an ice bath. The cooled solution is filtered and the resulting yellow-orange crystals which are formed (31 g) are dried.

After a further recrystallization in 1,2-dichloro ethane, 25 g of 1,8-dihydroxy-10-cyclohexylcarbonyl anthrone having a melting point of 220 ° C. are obtained.

Elemental Analysis: $C_{21}H_{20}O_4$: Calculated: C: 74.98; H: 5.99; O: 19.03. Found: C: 74.78; H: 5.91; O: 19.22.

(b) 1-hydroxy-8-acetoxy-10-cyclohexylcarbonyl anthrone

A solution of 5 g of 1,8-dihydroxy-10-cyclohexylcarbonyl anthrone, obtained above, in 100 cm$^3$ of acetic anhydride, protected from light and the humidity of the air, is brought with stirring to a temperature of 90° C. for three hours. The solution is then concentrated under reduced pressure. The resulting product is dissolved in 50 cm$^3$ of methylene chloride and introduced into a silica gel column. On elution with methylene chloride and evaporation of the elution phases, there are isolated, beginning with the first fractions, 1.2 g of the nontransformed initial reactant.

The subsequent fractions are concentrated yielding 1.5 g of 1-hydroxy-8-acetoxy-10-cyclohexylcarbonyl anthrone.

On recrystallization in a toluene-hexane mixture, there are obtained, after drying, 1.1 g of yellow crystals having a melting point of 154° C.

Elemental analysis: $C_{23}H_{22}O_5$: Calculated: C: 73.00; H: 5.86; O: 21.14. Found: C: 73.08; H: 5.85; O: 21.15.

EXAMPLE 3

Preparation of 1-hydroxy-8-isobutyryloxy-10-propionyl anthrone (a) 1,8-dihydroxy-10-propionyl anthrone To a suspension of 56.6 g (0.25 mole) of purified anthralin in 1750 cm$^3$ of anhydrous toluene, there are added at ambient temperature 27.3 cm$^3$ of anhydrous pyridine (0.34 mole) and then, slowly, over about a 20 minute period, 26.2 cm$^3$ of propionyl chloride (0.3 mole) are added. The mixture is then heated to 85° C. for about 1 hour. After return to ambient temperature, there are added to the reaction mixture 27.3 cm$^3$ of pyridine and 26.2 cm$^3$ of propionyl chloride. This mixture is then heated for 1 hour at a temperature of about 85° C.

The precipitated pyridinium hydrochloride is filtered, then washed with toluene. The toluene filtrates are concentrated to about 1 liter, then washed and dried on magnesium sulfate. The resulting solution is then chromatographed on silica gel column using initially as the eluant a mixture of hexane and toluene, and then toluene.

After evaporation of the various fractions, those containing 1,8-dihydroxy-10-propionyl anthrone are collected and dissolved at ambient temperature in toluene. On addition of hexane, the expected product precipitates and is isolated by filtration.

After drying, 54.6 g of pale yellow crystals of 1,8-dihydroxy-10-propionyl anthrone having a melting point of 154° C. are obtained.

Elemental analysis: $C_{17}H_{14}O_4$: Calculated: C: 72.33; H: 4.99. Found: C: 72.14; H: 5.06.

(b) 1-hydroxy-8-isobutyryloxy-10-propionyl anthrone.

A stirred solution of 10 g of 1,8-dihydroxy-10-propionyl anthrone, obtained above, in 50 cm³ of isobutyric anhydride, placed in an inert atomsphere and out of contact with light, is treated for 2 hours at a temperature between 100° and 120° C. The solution is then concentrated under reduced pressure.

The resulting product is then dissolved in 50 cm³ of methylene chloride and the solution is introduced into a silica gel column. On elution with methylene chloride, unreacted initial reactant is initially isolated, followed by the isolation of the expected product.

After evaporation of the elution phases 2.5 g of a residue are obtained. The residue is recrystallized in isopropyl ether, yielding 1.5 g of 1-hydroxy-8-isobutyryloxy-10-propionyl anthrone in the form of a yellow solid having a melting point of 111° C.

Elemental analysis: $C_{21}H_{20}O_5$: Calculated: C: 71.57; H: 5.73; O: 22.70. Found: C: 71.27; H: 5.84; O: 22.89.

EXAMPLE 4

Preparation of 1-hydroxy-8-acetoxy-10-propionyl anthrone

A solution of 3 g of 1,8-dihydroxy-10-propionyl anthrone obtained in Example 3(a) in 30 cm³ of acetic anhydride is treated for 2 hours with stirring and in the absence of light and the humidity of air, at a temperature between 90° C. and 100° C.

The solution is then evaporated under reduced pressure and the resulting product is dissolved in methylene chloride.

The solution is then introduced into a silica gel column. On elution with methylene chloride, there is isolated at the head of the chromatograph 0.8 g of the nontransformed initial reactant, followed by the isolation of expected product. After evaporation of the solvent and recrystallization in a hexanemethylene chloride mixture 1.5 g of 1-hydroxy-8-acetoxy-10-propionyl anthrone in the form of yellow crystals having a melting point of 106° C. are obtained.

Elemental analysis: $C_{19}H_{16}O_5$: Calculated: C: 70.36; H: 4.97; O: 24.67. Found: C: 70.47; H: 4.95; O: 24.48.

EXAMPLE 5

Preparation of 1-hydroxy-8-propionyloxy-10-propionyl anthrone

A solution of 100 g of 1,8-dihydroxy-10-propionyl anthrone, obtained in Example 3(a), and 100 cm³ of propionyl chloride in 1300 cm³ of anhydrous toluene is treated, with stirring and in the absence of light, at a temperature of 80° C. for 4 hours and left overnight at ambient temperature. 50 cm³ of additional propionyl chloride are added and the mixture is treated for 8 hours at 80° C. The reaction mixture is directly concentrated under reduced pressure, then taken up in 300 cm³ of methylene chloride. The methylene chloride phase is washed with water, dried on magnesium sulfate and introduced into a silica gel column.

On eluting with methylene chloride, there is isolated at the head of the chromatography 17 g of nontransformed initial reactant, then finally 37 g of the expected product. After two recrystallizations in isopropyl ether, 25 g of 1-hydroxy-8-propionyloxy-10-propionyl anthrone in the form of yellow crystals having a melting point of 125° C. are obtained.

Elemental analysis: $C_{20}H_{18}O_5$: Calculated: C: 70.99; H: 5.36; O: 23.64. Found: C: 71.16; H: 5.28; O: 23.76.

EXAMPLE 6

Preparation of 1-hydroxy-8-isobutyryloxy-10-cyclohexylcarbonyl anthrone

A solution of 5 g of 1,8-dihydroxy-10-cyclohexylcarbonyl anthrone, obtained in Example 2(a), in 100 cm³ of anhydrous toluene and 15 cm³ of isobutyric anhydride is treated, under an inert atmosphere, at reflux of the toluene for 6 hours. The mixture is introduced into a silica gel column and eluted with methylene chloride. A portion of the anhydride and isobutyric acid are removed. After concentration of the elution phases, a portion of the nontransformed initial reactant crystallizes, and is filtered and dried, thus isolating 1 g of the initial reactant. The filtrate is again introduced into a silica gel column and eluted initially with toluene and then with toluene-methylene chloride mixtures containing, respectively, 20%, 50% and 75% methylene chloride and finally with pure methylene chloride. The fractions containing the expected product are collected, then concentrated to dryness, yielding 1.5 g of the crude product. On recrystallization in a toluene-hexane mixture 1 g of 1-hydroxy-8-isobutyryloxy-10-cyclohexylcarbonyl anthrone in the form of yellow crystals having a melting point of 146° C. is obtained.

Elemental anaylsis: $C_{25}H_{26}O_5$: Calculated: C: 73.86; H: 6.45; O: 19.68. Found: C: 74.15; H: 6.49; O: 19.40.

EXAMPLES OF PHARMACEUTICAL AND COSMETIC COMPOSITIONS

EXAMPLE 1

Non-soluble 0.5 g tablet

| | |
|---|---|
| 1-hydroxy-8-propionyloxy-10-propionyl anthrone | 0.100 g |
| lactose | 0.082 g |
| stearic acid | 0.003 g |
| purified talc | 0.015 g |
| sweetening agent, sufficient amount | |
| coloring agent, sufficient amount | |
| rice starch, sufficient amount for | 0.500 g |

This tablet is prepared by directly compressing to dryness a mixture of the above components.

EXAMPLE 2

Non-soluble 0.8 g tablet

| | |
|---|---|
| 1-hydroxy-8-isobutyryloxy-10-propionyl anthrone | 0.200 g |
| lactose | 0.200 g |
| gum arabic (20% in water) | 0.080 g |
| liquid paraffin | 0.004 g |
| purified talc | 0.016 g |
| starch, sufficient amount for | 0.800 g |

This tablet is prepared by wet grinding the mixture of 1-hydroxy-8-isobutyryloxy-10-propionyl anthrone, starch lactose and 20% gum arabic in water.

The granular mixture is then dried and sieved, the granules resulting from the sieving operation then being mixed with the paraffin and talc.

EXAMPLE 3

Granules in a 3 g packet

| | |
|---|---|
| 1-hydroxy-8-acetoxy-10-propionyl anthrone | 0.150 g |
| sucrose | 2.220 g |
| methyl cellulose | 0.030 g |
| purified water | 0.600 g |

The paste obtained by mixing the above four components is wet granulated and then dried.

EXAMPLE 4

1 g capsules containing 0.05 of the active component

Capsule content: oily suspension

| | |
|---|---|
| 1-hydroxy-8-acetoxy-10-cyclohexycarbonyl anthrone | 0.050 g |
| cod liver oil, sufficient amount for | 0.500 g |

The envelope of the capsule is produced by molding, then drying an appropriate mixture of gelatin, glycerine, water and preservative. The above suspension is introduced into the capsule which is then sealed.

EXAMPLE 5

Gelule containing 0.3 g of powder

Composition of the powder

| | |
|---|---|
| 1-hydroxy-8-propionyloxy-10-propionyl anthrone | 0.080 g |
| cornstarch | 0.060 g |
| lactose, sufficient amount for | 0.300 g |

The above powder is packaged in a gelule composed of gelatin, titanium dioxide and a preservative.

EXAMPLE 6

Hydrophobic ointment

| | |
|---|---|
| 1-hydroxy-8-propionyloxy-10-anthrone | 1.00 g |
| petrolatum | 49.00 g |
| ceresin | 15.00 g |
| petrolatum oil | 35.00 g |

EXAMPLE 7

Non-ionic emulsion for topical application

| | |
|---|---|
| 1-hydroxy-8-isobutyryloxy-10-propionyl anthrone | 0.70 g |
| anhydrous eucerin | 70.00 g |
| petrolatum oil | 10.00 g |
| preservative, sufficient amount | |
| sterile demineralized water, sufficient amount for | 100.00 g |

For good preservation, this emulsion should be stored in the absence of heat and light.

EXAMPLE 8

Anhydrous gel

| | |
|---|---|
| 1-hydroxy-8-propionyloxy-10-propionyl anthrone | 1.50 g |
| silica, sold under the trade name "Aerosil 200" by Degussa | 7.00 g |
| isopropyl myristate, sufficient amount for | 100.00 g |

EXAMPLE 9

A two-part milk composition to be emulsified at the time of use

First Part

| | |
|---|---|
| 1-hydroxy-8-propionyloxy-10-propionyl anthrone | 2.00 g |
| triglycerides of capric/caprylic acid, sold under the trade name "Miglyol 812" by Dynamit Nobel, sufficient amount for | 20.00 g |

Second Part

| | |
|---|---|
| Sorbitan monooleate polyoxyethylenated with 20 moles of ethylene oxide, sold under the trade name "Tween 80" by Atlas | 10.00 g |
| preservatives, sufficent amount | |
| sterile demineralized water, sufficient amount for | 80.00 g |

The first part is stirred so as to suspend the active component therein. Thereafter the two parts are mixed together before using the resulting milk.

EXAMPLE 10

Stick

| | |
|---|---|
| 1-hydroxy-8-propionyloxy-10-propionyl anthrone | 5.00 g |
| cocoa butter | 12.50 g |
| ozokerite wax | 18.50 g |
| refined white paraffin | 6.25 g |
| petrolatum oil | 12.75 g |
| isopropyl myristate, sufficient amount for | 100.00 g |

EXAMPLE 11

Antipellicular and anti-hair-fallout capillary composition.

| | |
|---|---|
| 1-hydroxy-8-acetoxy-10-cyclohexylcarbonyl anthrone | 0.50 g |
| stannous chloride | 0.30 g |
| isopropyl myristate, sufficient amount for | 100.00 g |

What is claimed is:

1. 1-hydroxy-8-acyloxy-10-acyl anthrone having the formula

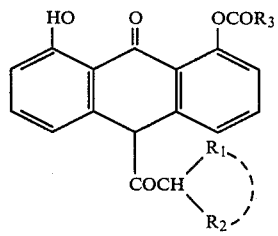

wherein $R_1$ represents hydrogen or linear lower alkyl, $R_2$ represents hydrogen, linear or branched alkyl having 1–6 carbon atoms, or linear or branched alkenyl having 2–6 carbon atoms, or $R_1$ and $R_2$ together with the carbon atom to which they are attached form a cycloalkyl radical having 3–6 carbon atoms, $R_3$ represents linear or branched alkyl having 1–6 carbon atoms, linear or branched alkenyl having 2–6 carbon atoms, cycloalkyl having 3–6 carbon atoms.

2. The compound of claim 1 wherein each of $R_2$ and $R_3$ as linear or branched alkyl is selected from the group consisting of methyl, ethyl, propyl, isopropyl, butyl, isobutyl, tert.butyl, pentyl and isopentyl.

3. The compound of claim 1 wherein each of $R_2$ and $R_3$ as linear or branched alkenyl is selected from the group consisting of allyl, 1-propenyl and 2-propenyl.

4. The compound of claim 1 wherein said cycloalkyl is cyclopentyl or cyclohexyl.

5. The compound of claim 1 selected from the group consisting of
1-hydroxy-8-acetoxy-10-acetyl anthrone,
1-hydroxy-8-acetoxy-10-cyclohexylcarbonyl anthrone,
1-hydroxy-8-isobutyryloxy-10-propionyl anthrone,
1-hydroxy-8-acetoxy-10-propionyl anthrone,
1-hydroxy-8-propionyloxy-10-propionyl anthrone, and
1-hydroxy-8-isobutyryloxy-10-cyclohexylcarbonyl anthrone.

6. A cosmetic or pharmaceutical composition comprising in an appropriate vehicle an effective amount of, as an active component, the compound of claim 1.

7. The composition of claim 6 wherein said active component is present in an amount between 0.1 and 5 percent by weight based on the total weight of said composition.

* * * * *